United States Patent [19]

Synek

[11] 4,348,385

[45] Sep. 7, 1982

[54] FLOWABLE PESTICIDES

[75] Inventor: Joseph Synek, Overland Park, Kans.

[73] Assignee: Mobay Chemical Corporation, Pittsburgh, Pa.

[21] Appl. No.: 207,318

[22] Filed: Nov. 17, 1980

[51] Int. Cl.$^3$ ...................... A01N 25/22; A01N 57/00
[52] U.S. Cl. ..................................... 424/173; 424/200; 424/220; 424/222; 424/249; 424/274; 424/286; 424/300; 424/326
[58] Field of Search ............... 424/200, 173, 220, 222, 424/249, 274, 286, 300, 326

[56] References Cited

U.S. PATENT DOCUMENTS

| | | | |
|---|---|---|---|
| 2,758,115 | 8/1955 | Lorenz | 260/248 |
| 3,060,084 | 10/1962 | Littler | 167/42 |
| 3,342,581 | 9/1967 | Woodward et al. | 71/65 |
| 3,399,991 | 9/1968 | Littler | 71/120 |
| 3,689,245 | 9/1972 | Weidman et al. | 71/65 |
| 3,737,551 | 6/1973 | Karsten et al. | 424/286 |
| 3,791,811 | 2/1974 | French et al. | 71/120 |
| 3,920,442 | 11/1975 | Albert et al. | 71/92 |
| 4,000,258 | 12/1976 | Shieh et al. | 424/93 |

OTHER PUBLICATIONS

The Pesticide Chem. News Guide–Food Chemistry News Guide, 12/78, p. 112.
Toxicology & Applied Pharmacology, vol. 47 (1979) pp. 451–460.

*Primary Examiner*—Leonard Schenkman
*Attorney, Agent, or Firm*—Gene Harsh

[57] ABSTRACT

A storage stable, flowable, water dispersible pesticide suspension in an organic water miscible solvent displaying significant but limited solvation of the biologically active pesticide compound and a procedure for preparing it are disclosed. The suspension is stabilized against Ostwald ripening with a dispersant, preferably solid ionic dispersant, and contains inert solid fillers to control the viscosity of the suspension. The particle size of the solid ingredients are controlled to prevent agglomeration.

9 Claims, No Drawings

FLOWABLE PESTICIDES

FIELD OF THE INVENTION

Flowable biologically active pesticide formulations which are readily dispersible in water and which have good storage stability and resistance to crystallization upon exposure to depressed temperatures are disclosed.

BACKGROUND OF THE INVENTION

There are two distinct major fields of endeavor related to the utilization of chemicals effective to combat biological pests, whether plant or animal. The first is the discovery and development of chemical compounds and mixtures of such compounds which selectively adversely affect the pest without damaging the environment to be protected, particularly harvestable crops, livestock or ornamental plants. The other is the development of methods of applying appropriate dosages of such so-called "biologically active" compounds to the target host in an efficient and economical manner. Such methods include the use of formulations which include ingredients chemically inert to both this target host and the pest to be controlled as well as to the "active ingredient." These "inert" ingredients are effective in determining the physical characteristics of the total formulation.

A particularly useful formulation is one in which the "active ingredient" can be readily dispersed in water or a primarily aqueous medium. The end-user can then readily prepare suspensions and apply them to the target host in the appropriate dosage by controlling the amount of dilution with water. Ideally, the "active ingredient" should itself be readily soluble in water but unfortunately very few of the compounds of interest as pesticides are or can be altered to be sufficiently water soluble, at least not without adversely affecting their cost or biological efficiency. Therefore, the practice has developed of combining or formulating these compounds with "inert" ingredients to facilitate their dispersibility in water.

Such water dispersible formulations have generally been prepared by combining the "active ingredients," an emulsifier or wetting agent, a dispersant and an "inert" carrier or filler material. This last material has been found necessary in order to obtain a suitable admixture of the emulsifier, dispersant and active ingredients and to facilitate the size reduction of these ingredients to an appropriate particle size, e.g., in a hammer mill or ball mill. This carrier material may be either a solid or a liquid. The former type of formulations include wettable powders such as those discussed in U.S. Pat. No. 3,737,551, although other types of solid formulations such as the water dispersible granules of U.S. Pat. No. 3,920,442 have been proposed to overcome the disadvantages of handling fine powders. The latter type of formulations include flowables in which the major dispersing medium is water, such as those disclosed in U.S. Pat. No. 3,060,084. Typical of such products are SENCOR herbicide marketed by Mobay Chemical Corporation, SEVIN insecticide marketed by Union Carbide and FURADAN insecticide marketed by FMC.

Formulations are also available in which the "active ingredient" is dispersed in a petroleum distillation product. Normally, such formulations are not dilutable with water but find application in low or ultra-low volume applications. Typical of such products are SEVIN oil insecticide marketed by Union Carbide and DYLOX 1.5 oil insecticide marketed by Mobay Chemical Corporation. The latter product is interesting in that its active ingredient is also available in a water soluble powder formulation.

Not all pesticidally active compounds are amenable to formulation in a water-based flowable composition. In particular, the compound may not have long term stability in the presence of water but may hydrolyze or it may be difficult to prepare stable dispersions with suitable viscosities. In such cases, the compound may be dissolved in an organic solvent which also contains emulsifier but, in such cases, the stability of the solution becomes of concern. If the concentration of the solution is sufficiently high (and the economic incentive is to minimize the biologically ineffective solvent), crystallization may occur at normally encountered field temperatures and redissolution may not be readily achieved. Such crystallization may also occur when the formulation is combined with cold water resulting in plugged feed lines or spray nozzles in the application equipment. In addition, these solvent diluents may render the formulation incompatible with other pesticides with which it may be desirable to apply it. Finally, many of the solvents suitable for many active compounds of interest pose environmental problems.

As discussed hereinabove, formulations have been prepared in media in which the active compounds are almost totally insoluble (less than 100 ppm is usually recommended) but unfortunately for many such compounds, these media are not readily emulsifiable with water. An interesting exception is the formulation of Sevin insecticide and a dispersant in molasses which while being water miscible is believed to have no solubility for the active compound. On the other hand, many of the media which do display suitable compatibility with water and particularly those which are miscible with water also display sufficient solvation for active compounds of commercial interest to give rise to the problem of "Ostwald ripening." This phenomenon, beneficially utilized in the field of photographic emulsions, results when the smaller particles in a suspension dissolve in the suspending medium and then crystallize out on the larger particles, thus increasing the average particle size of the suspension until it ultimately becomes unstable and precipitates or separates from the medium. However, a formulation of what is believed to be metribuzin and lignin sulfonate dispersant in a 6:1 water/propylene glycol medium has been introduced ito the market and appears to form a stable dispersion in spite of metribuzin's solubility of 1200 ppm in water.

A technique has now been discovered to suppress this phenonmenon and prepare stable suspensions of active compounds in media in which they have significant solubility. Thus, these compounds can be suspended in media which are readily emulsifiable with water or even miscible with water.

The media utilized in the present invention have been used as carriers or diluents for biologically active ingredients. U.S. Pat. No. 4,000,258 discloses suspensions of an insecticidally active microorganism in various alcohols and, in some cases, these suspensions also include surfactants which aid water dispersibility or which reduce the suspension's tendency to settle. While the suspended ingredient is present in finely divided form, its solubility, if any, in the carrier is not reported. An article in *Toxicology and Applied Pharmacology,* Vol. 47, pages 451 to 460 (1979) reports the use of propylene glycol to "suspend" a variety of insecticides for a 24-hour exposure test. Some of the "suspended" insecticides are reported to be miscible with propylene glycol while others are not reported to be soluble in this solvent. There does not, however, appear to be any recognition that dispersants and inert fillers can be combined with a solid active ingredient to prepare a suspension having long term stability using a liquid medium in which the active ingredient has significant solubility.

A particularly attractive insecticide which displays these problems is Azinphos-methyl disclosed in U.S. Pat. No. 2,758,115 and more formally described as o,o-dimethyl s-[(4-oxo-1,2,3-benzotriazin-3(4H)-yl)methyl]-phosphorodithioate:

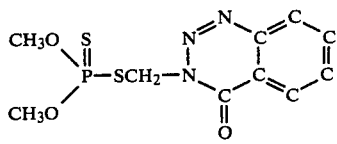

Formulations of this compound dissolved in aromatic petroleum fractions lose cold storage stability at temperatures of between 15° C. and 0° C. and tend to crystallize when combined with water at temperatures below about 15° C. Furthermore, these formulations are incompatible when tank mixed with other pesticides registered with the EPA for the same crops such as BRAVO 6 fungicide marketed by Diamond Shamrock and BENLATE 50 fungicide marketed by DuPont, although this same compound when formulated as a wettable powder is compatible with these same pesticides. On the other hand, this wettable powder formulation is incompatible with such pesticides as BOLSTAR 6 insecticide marketed by Mobay Chemical Corporation and suitable for cotton as is Azinphos-methyl.

SUMMARY OF THE INVENTION

The present invention is concerned with flowable water dispersible pesticide formulations. These formulations comprise a solid, finely divided, partially water insoluble or water sensitive biologically active compound, an organic water compatible solvent in which the active compound has some solubility and sufficient inert finely divided filler and water active dispersant to maintain the active compound in a stable dispersion in the organic solvent. The solvent preferably dissolves less than 10 parts of active compound per 90 parts of solvent, more preferably less than 5 parts per 95 and most preferably less than 2 parts per 98 at 40° C. The solvent should be readily miscible with water in a wide range of proportions. The filler material should be chemically inert to the active compound, substantially insoluble in the organic solvent and in a finely enough divided form to be readily dispersed in the solvent. The dispersant may be any of the compounds known to the art for their ability to promote the dispersion of water insoluble solids in water. These dispersants are to be distinguished from emulsifiers or wetting agents whose primary function is to decrease the surface tension between water and hydrophobic particles. Typical dispersants suitable for use in this invention do not significantly affect this surface tension; are solid at room temperature in pure form; and carry ionic groups on their molecules. These components are used in such proportions that the organic solvent forms the continuous phase and the active compound is stably dispersed therein.

The present invention is also concerned with a process for preparing flowable water dispersible pesticide formulations by combining the hereinabove recited ingredients. The biologically active compound may conveniently be combined with the organic solvent, inert filler and dispersant in a single step or by sequential addition. The active compound may be size reduced to yield a suitable particle size distribution to form a stable suspension before combination with the organic solvent or preferably after such combination. The inert filler is usually obtained with a suitable size distribution, although it can be size reduced with the active compound. The active compound is preferably either purified before combination with the organic solvent or a portion of the inert filler is provided with sufficient surface adsorbtivity to remove any impurities which would significantly impair the stability of the suspension in the organic solvent. The size reduction and combining operations should be conducted in such a manner as to avoid melting the active compound or sufficient inert filler with surface adsorbtivity should be provided to take up substantially all of the active compound which is melted.

A preferred composition comprises active compound and organic solvent in a ratio between 1:18 and 4:1 with the amount of inert filler and dispersant combined being less than the amount of active compound. In a particularly preferred composition, both the active compound and inert filler have particle distributions with substantially no particles in excess of 12 microns.

DETAILED DESCRIPTION OF THE INVENTION

The biologically active compound with which the present invention finds utility should be solid at room temperature; be partially insoluble in water or chemically unstable upon long term exposure to water; and be somewhat soluble in an organic water compatible solvent. The specific biological activity of these compounds is not important but rather its physical properties. Included among the suitable compounds are insecticides such as Azinphos-methyl and PROPOXUR; herbicides such as METRIBUZIN; and bird repellants such as Methiocarb (MESUROL repellant) Of particular interest is the Azinphos-methyl.

These compounds share the common feature that it is not feasible to dilute them with water and obtain formulations which display long-term stability. The difficulty with hydrolytically sensitive compounds such as Methiocarb is self-evident but an intermediate degree of solubility in water also poses a problem. If the solubility is too limited to allow the preparation of solutions in commercially acceptable strengths but in excess of about 100 ppm, suspensions in water tend to be unstable. This is believed to be due to the mechanism of "Ostwald ripening" discussed hereinabove. Because of the expense of transporting and storing formulations with high concentrations of water, formulations with less than about 2.5 wt. % of active ingredients are unattractive. Therefore, the present invention finds particular utility with active compounds which have organic solvent solubilities between 100 ppm and 20 parts per 80 of organic solvent, more particularly those with solubilities between 500 ppm and 2.5 parts per 97.5 of organic solvent at 20° C.

The active compound should be sufficiently finely divided to form a stable suspension in the organic solvent when combined with the dispersant and inert filler. It is preferred that it have a particle size distribution with substantially no particles in excess of about 20 microns, preferably about 12 microns. It is particularly advantageous if no more than 40% of the particles are in excess of about 8 microns, preferably 4 microns.

The active compound may be size reduced by any of the well-known techniques such as hammer milling, air milling, ball milling, bead milling, treatment in an attritor and sand milling, such as described in U.S. Pat. No. 2,581,414. If the compound has a melting point sufficiently low that some of it may be melted during the size reduction, a grinding aid is usually employed. Typically, it is a particulate material with an elevated melting point and a high surface adsorptivity such as a silica which can absorb up to five times its own weight, diatomaceous earth, fuller's earth or bentonite. The surface adsorptivity and amount should be balanced against the degree of melting likely to occur and the presence of any impurities initially admixed with the active compound as a result of its commercial synthesis.

This grinding aid may conveniently provide a portion of the inert filler required to maintain the stability of the suspension but it is preferred to minimize the content of such adsorptive materials in order to avoid adsorbing excessive amounts of the suspension medium. The amount necessary may be reduced by purifying the active compound by known techniques such as recrystallization.

The "grinding aid" may be dispensed with if the active compound is sufficiently pure and if it has suitable physical characteristics, particularly a sufficiently high melting point to permit the required size reduction. An example of such a compound is Metribuzin with a melting point of 125° C. On the other hand, a compound such as Azinphosmethyl with a melting point of 73° C. in the pure state is more conveniently size reduced with the aid of such a grinding aid.

The organic solvents suitable for use in the present invention should have a limited solubility for the active compound and should be readily emulsifiable with water. If the solubility is too great, an excessive amount of dispersant and inert filler will be required to maintain the stability of the suspension. Naturally, the inventive concept is not involved if the solvent has a solubility for the active compound of less than about 100 ppm, since the problem of "Ostwald ripening" is not involved. The motivation for using solvents having solubilities in excess of that traditionally tolerated in suspension media is to have media readily emulsifiable with water. It is preferred that these solvents be emulsifiable without the aid of any emulsifiers or wetting agents and particularly preferred that they be miscible with water. Included among such solvents are the glycols such as ethylene glycol and propylene glycol, glycerol, isopropyl alcohol, butyro lactone, cyclohexanone, tetrahydrofuranyl alcohol and low molecular weight polyalkylene glycols with ethylene glycol being preferred and propylene glycol being especially preferred.

The solvents should, of course, be chemically inert to the active ingredient and have a minimal, if any, effect on the environment to which the formulation is to be applied. The latter requirement may cause certain solvents to be unsuitable for use in certain applications.

The solvents must be liquid at room temperature and preferably remain liquid at temperatures below 0° C. The lower the freezing point of the solvent, the greater the suspension's stability to the low temperatures which may be encountered under field conditions. It is further preferred that the solvents have vapor pressures less than that of water. In such cases, the suspensions are especially suitable for use as low or ultra-low volume direct spray formulations.

The dispersants suitable for use with this invention are those materials which reduce the cohesiveness of like particles and particularly those materials which are known to aid in the dispersion of insoluble solids in water. It is preferred to use dispersants which are solid in their pure state although they may be commercially available in aqueous solution. Liquid dispersants are disfavored because of the danger that the dispersant itself will act as a solvent for the active compound and thus adversely affect the stability of the suspension. A particularly suitable class of dispersants are those which carry ionic groups, particularly anionic groups. Included within this group are the lignin sulfonates, the metal salts of naphthylene sulfonic acid formaldehyde condensates and carboxylated polyelectrolytes. These "dispersants" are to be distinguished from the so-called "wetting agents" or "emulsifiers" whose primary purpose is to reduce the surface tension between water and a hydrophobic solid. Although "dispersants" which have this effect may be suitable, they are not selected on this basis and it is preferred that the "dispersants" have no significant effect on this surface tension. The lignin sulfonates are particularly preferred, particularly the alkali metal sulfonates and especially the sodium sulfonates.

The amount of dispersant needed is dependent upon the solubility of the active compound in the suspending medium and the amount of inert diluent or filler utilized. The higher the solubility or the lower the filler content, the more dispersant which is required to maintain a stable suspension. Of course, the effectiveness of the dispersant per unit weight must also be taken into consideration. In general, between about 1 and 5% based on the weight of solids (active compound, dispersant, inert filler and any other additive) has been found suitable. However, an appropriate amount for any given system can readily be determined by employing the concepts of this invention and testing formulations with increasing amounts until a stable suspension is obtained.

The inert diluent or filler can, in principle, be any room temperature solid which is chemically inert to the other ingredients and insoluble (preferably less than 100 ppm) in the suspension medium or solvent. It is preferable that it have a sufficiently high melting point to avoid melting during normal grinding or other mechanical size reduction processes and particularly preferred that it readily cleave at room temperature. It may be initially obtained in a sufficiently finely divided state to stably disperse in the suspending medium or it may be size reduced with the active ingredient.

A portion of this inert filler may be provided with a high surface adsorptivity, which is conveniently defined as the weight of materials the filler can adsorb based on its own weight. Suitable materials range from the very high surface area silicas which can adsorb up to five times their own weight through the diatomaceous earths and fuller's earths, the absorbent clays to the bentonites which absorb about 20% of their own weight. The amount of such material should be limited because it can often adsorb suspending medium as well as impurities and melted active compound. It is preferred that the amount of such materials is balanced against the needed adsorptive capacity. Obviously, this implies that less of a more adsorptive material may be utilized. Naturally, no adsorptive filler at all need be utilized with the fairly pure high melting point active compounds such as Metribuzin (125° C.). With the lower melting point compounds such as Azinphos-methyl (73° C.), it is convenient to use at least sufficient adsorbent to take up all of the compound, particularly if it contains impurities from its synthesis. A suitable range has been found to be from 25 to 100 parts per 100 parts of active compound, particularly with a high surface area silica. Such high adsorbtivity materials are preferred from the standpoint of minimizing the amount of inactive compounds of the formulation but such considerations may be counterbalanced by the higher cost of the higher adsorptivity materials.

The balance of the inert filler need have no special properties other than being a solid inert diluent for the active compound. However, it is preferred that it be as inexpensive as possible and be chemically inert to the target environment. Included among such materials are talcs, kaolin and other non-absorbent clays, as well as the lower surface area silicas.

The amount of inert filler utilized will depend on the nature of the suspending medium, the amount of dispersant utilized and the amount of adsorbent filler needed. The lower the solubility of the active compound in the medium, the lower both the amount of diluent and the amount of dispersant required and this is particularly true when the suspending medium does not wet the active compound. In sufficiently high amounts, the dispersant can serve as the diluent or inert filler as well but this is generally economically unattractive and may also be undesirable because the biological inertness of some dispersants is lost at higher concentrations. In general, the amount of inert filler including the adsorptive filler may range from 25 to 100 parts per 100 parts of active compound.

The suspensions of the present invention may also contain other ingredients known in the pesticide formulation art. In particular, they may contain a wetting agent or emulsifier, which is to be distinguished from the required dispersant. These wetting agents are known for their ability to decrease the surface tension between water and a hydrophobic phase. Typically they are liquid at room temperature and include the detergents which have both hydrophilic and lipophylic portions to their molecules. Although it is generally acknowledged that these wetting agents produce an effect opposite to that of a dispersant, there are some compounds that to some extent provide both effects. Such compounds may be utilized as to the required dispersant of the present invention. However, in general, wetting agents may have an adverse effect on the dispersing effect of the dispersant in water and should be selected so as not to adversely effect the stability of the suspension after emulsification with water. It is believed that since such agents are not designed to effect the surface tension of the suspending medium, the suspensions can readily tolerate such ingredients. In general, amounts up to the amount of dispersant may be conveniently utilized although no amount is actually required. Amounts between about 1 and 5 parts per 100 of active ingredient are suitable.

The total formulation is preferably readily flowable at room temperature and preferably it should contain at least 2.5 parts of active compound per 100 parts of formulation. Such flowables should have a viscosity of less than about 5000 centipoise at 20° C., preferably between about 400 and 2000 cps. However, the viscosity should be balanced with the amount and nature of both the active compound and the other solid ingredients. However, useful suspensions can also be prepared which are essentially pastes. Furthermore, some of the suspensions of this invention may be sufficiently thioxtropic that before the application of some shear as by shaking they are essentially pastes.

The preferred formulations or suspensions are stable to both long term exposure at depressed temperatures and cycling between such depressed temperatures and the highest temperatures encountered in the field. These two criteria are independent and one may be met while the other is not. It is believed that as the temperature is decreased, the decreasing solubility of the active compound may cause some of it to crystallize out of solution and that such crystal growth per se or its nucleation on the suspended particles of active compound may be sufficient to destabilize the suspension. But even if the crystallization of some of the active ingredient initially in solution is not sufficient to result in destabilization, it is believed that reheating of the suspension after such crystallization may cause dissolution of the smaller suspended particles of active compound. Some of this newly dissolved material may then crystallize on cooling. Because nucleation of such particles on already existing particles will be favored, the net result will be a change in the particle size distribution to larger particles until the suspension is destabilized.

The former property may be conveniently evaluated by storage at 20° or 32° F. for periods from 3 days up to one year while the latter may be evaluated by cycles of storage at such depressed temperatures for periods ranging from 3 days upwards, heating to room temperature (e.g., 20° C.) and returning to the colder temperatures. Some minimum storage time at depressed temperatures is important because while decreases in temperatures decrease solubility they also decrease the kinetic rate at which crystal growth occurs. Therefore, a suspension which is unstable at a given temperature may display short term stability because there is insufficient time for equilibrium to be reached. The ultimate test of course is subjection to the thermal history encountered by a formulated pesticide in commercial use, i.e., the thermal cycling actually encountered in the field.

The need for stability over a range of temperatures implies that the viscosity must be adjusted so that the minimum necessary for stability is maintained over this same range. Typically although not universally, the viscosity decreases with increasing temperature so that the formulation must provide this viscosity at the highest temperature to which the suspension is exposed. If the suspending medium is combined with the active compound before the active compound is size reduced, this may be the temperature obtained during or immediately after size reduction. This viscosity is dependent upon the relative densities of the suspending medium and the solid ingredients. If they are fairly closely matched, a fairly low viscosity may be sufficient. On the other hand, a significant mismatch may require somewhat higher viscosities, e.g., Azinphos-methyl with a density of greater than 10 lb/gallon suspended in propylene glycol which has a density of 8.6 lb/gallon.

This viscosity may conveniently be controlled by the solid formulation ingredients other than the active compound. Preferably, it is controlled primarily by the amount and nature of the inert filler. As discussed hereinabove, the adsorptive fillers can adsorb some of the suspending medium thus effectively increasing the viscosity. The particle size distribution of all the solid ingredients may also have an effect because generally the smaller the particle size, the higher the particle surface area and viscosity of the suspension for the same volume of particles. However, the particle size is chosen primarily by the principle that smaller particles are generally more resistant to settling. The use of other additives such as thickening agents while not preferred, is not excluded.

A particularly preferred suspension is formed from Azinphos-methyl in propylene glycol. Such suspensions may have viscosities in excess of 600 cps at 20° C. and particle size distribution with 60% under 4 microns and less than 5% over 12 microns. The formulation also includes a dispersant, an adsorptive inert filler and a non-adsorptive inert filler. A particularly preferred version utilizes an ionic solid dispersant such as a sodium lignosulfonate, a high surface area silica and a non-adsorbent clay such as Barden clay. The dispersant is utilized in between 2 and 6 parts per 100 parts of Azinphos-methyl and the adsorptive silica is utilized between 15 and 50 parts per 100 parts of Azinphos-methyl.

The suspension also contains between 20 and 40 parts of Azinphos-methyl per 100 parts of total formulation and between 30 and 70 parts per 100 of propylene glycol. Such particularly preferred suspensions may be stable to one year at 0° F. and a one year exposure to the temperature profile of the temperature region of the United States.

This suspension is readily compatible with a number of other formulated active compounds even when combined in large amounts of water ("tank mixed"). It may also be combined with cold (0° C.) water without crystallization. It also remains readily pourable at temperatures well below 0° C.

The invention is further illustrated, but is not intended to be limited by the following examples in which all parts and percentages are by weight unless otherwise specified.

EXAMPLES

EXAMPLE 1

An insecticidal formulation was prepared by combining the following ingredients:
34.4 parts of Azinphos-methyl
5.0 parts of non-adsorptive amorphous silica diluent with a surface area of about 14,000 cm$^2$/g finer than 400 mesh Taylor screen (particle size maximum <10 microns)
1.0 parts of sodium isopropyl naphthalene sulfonate wetting agent
1.5 parts of sodium lignosulfonate dispersant
56.5 parts of propylene glycol solvent (suspending medium).

The ingredients were combined in a Waring blender and size reduced in a Reitz (hammer) mill to a 0.006" screen. Two subsequent passes through a sand mill with 2 mm beads gave a product having a viscosity of 660 cps at 20° C. and the following Coulter counter determined particle size distribution:

| 0–4 microns | 45.3% |
|---|---|
| 4–8 microns | 33.0% |
| 8–12 microns | 10.6% |
| >12 microns | 6% |

On mixing with hard water (1000 ppm salts) at 1:100 and with soft water (100 ppm salts) at 3.5:100, excellent dispersions were obtained.

The procedure was twice repeated with the addition of one pass through the sand mill with 1 mm beads. One of the resulting dispersions had a viscosity of 740 cps at 20° C. and the following Coulter counter determined particle size distributions were obtained:

| 0–4 microns | 61.9% | 58.4% |
|---|---|---|
| 4–8 microns | 28.9% | 28.6% |
| 8–12 microns | 7.1% | 9.1% |
| >12 microns | 2.0% | 3.8% |

On storage both at room temperature and about −6° C. these dispersions remained stable showing no evidence of precipitation after three days. The dispersion stored at −6° C. also remained stable on reheating to room temperature.

EXAMPLE 2

An insecticidal formulation was prepared from the following ingredients in a manner similar to Example 1:
23.3 parts of Azinphos-methyl
5.0 parts of same silica diluent as used in Example 1
1.0 parts of sodium isopropyl naphthalene sulfonate wetting agent
1.5 parts of sodium lignosulfonate dispersant
64.7 parts of propylene glycol.
The resultant dispersion was stable both at room temperature and −6° C. as well as upon cycling between these temperatures.

EXAMPLE 3

An insecticidal composition was prepared from the following ingredients:
21.6 parts Azinphos-methyl
11.2 parts of a sodium silica aluminate diluent with a mean particle size of 12 to 20 millimicrons and an average surface area of 180 to 225 m$^2$/g
1.6 parts of the amorphous silica diluent used in Example 1
1.2 parts of sodium isopropyl naphthalene sulfonate
1.5 parts of sodium lignosulfonate dispersant
3.2 parts of Barden clay.
After some size reduction this composition was combined with 61.4 parts of propylene glycol and further size reduced in a sand mill. These compositions were then evaluated for storage stability by observing the change in particle size distribution and occurrence of sedimentation under various conditions as follows:

| Coulter particle size distribution | Initial | 6 months at about 20° C. | 6 months ambient temperature Kansas City | 6 months at −6° C. |
|---|---|---|---|---|
| 0–4 microns | 82 | 83 | 80 | 84 |
| 4–8 microns | 14 | 14 | 16 | 14 |
| 8–12 microns | 3 | 2 | 3 | 1 |
| >12 microns | 1 | 1 | 1 | 0 |
| Occurrence of sediment | none | none | none | none |
| Thixotropic | no | yes | yes | no |

| Coulter particle size distribution | Initial | 6 months at about 20° C. | 6 months ambient temperature Kansas City | 6 months at −6° C. |
|---|---|---|---|---|
| gelling | | | | |

Within experimental error the particle size distribution was unchanged from the initial state. The thixotropic thickening was readily eliminated by shaking the container and the dispersion then became readily pourable.

EXAMPLE 4

A composition similar to that of Example 3 was prepared and evaluated in a similar manner with the following results:

| Coulter counter size distribution | Initial | 1 year ambient temperature Kansas City | 1 year −18° C. | 4 weeks 40° C. | 4 weeks −18° C. | 8 weeks 40° C. | 8 weeks −18° C. | 16 weeks 40° C. | 16 weeks −18° C. |
|---|---|---|---|---|---|---|---|---|---|
| 0–4 microns | 71 | 70 | 74 | 73 | 71 | 80 | 70 | 79 | 80 |
| 4–8 microns | 24 | 19 | 21 | 20 | 24 | 17 | 18 | 18 | 17 |
| 8–12 microns | 4 | 5 | 4 | 5 | 4 | 2 | 3 | 3 | 3 |
| >12 microns | 1 | 6 | 1 | 2 | 1 | 1 | 0 | 0 | 0 |
| Occurrence of sediment | none | none | none | none | none | none | none | none | none |
| Thixotropic gelling | no | yes | no | yes | no | yes | no | yes | no |
| Viscosity 23° C. in cps | 380 | 460 | 420 | 460 | 340 | 560 | 380 | — | — |

The viscosity was determined by the Brookfield technique and has a reliability of ±40 cps. The one year tests were in a 2½ gallon polyethylene jug and the shorter tests were in pint glass bottles.

EXAMPLE 5

A similar composition to that of Example 4 was prepared and evaluated in a similar manner except that the content of coarse particles was somewhat higher with the following results:

| Coulter counter size distribution | Initial | 2 months at 40° C. 5 gallon polyethylene pail | 2 months at 40° C. 2½ gallon polyethylene jug |
|---|---|---|---|
| 0–4 microns | 54 | 58 | 57 |
| 4–8 microns | 32 | 32 | 32 |
| 8–12 microns | 11 | 7 | 10 |
| >12 microns | 2 | 1 | 1 |
| Viscosity at 23° C. in cps | 960 | 820 | 860 |

EXAMPLE 6

A composition made to the formulation of Example 3 was found readily compatible with the following commercially available agricultural pesticides:

1. Ambush 2
2. BAYCOR 50% WP
3. Benlate 50
4. BOLSTAR 6
5. Bravo 500
6. Bravo 75
7. Captan 50 W
8. Cyprex 65 — Add Ortho X-77
9. DEF
10. Duter
11. DYRENE 50% WP
12. Fundal 4
13. Galecron 4
14. Maneb
15. Pounce 3.2
16. Pydrin 2.4 EC
17. Harvade
18. Orthene 75 SP
19. BOLSTAR + Fundal
20. BOLSTAR + Galecron

EXAMPLE 7

A composition formulated according to Example 3 was applied to a variety of agricultural crops alone and in combination with a variety of other agricultural pesticides. The pesticidal control was as good as and the phytotoxicity no worse than other commercially available formulations of Azinphos-methyl. Among the crops and pests successfully treated were the following:

| CROP | PESTS |
|---|---|
| Potatoes | Colorado potato beetle; potato flea beetle; |
| Cotton | Weevils |
| Apple | Green fruitworm |
| Cherry | Green fruitworm |
| Peaches | — |
| Tomato | — |
| Sugarcane | — |

EXAMPLE 8

A composition formulated according to Example 3 was compared to two commercially available Azinphos-methyl formulations on cotton and cucumber as follows:

| TREATMENT | OZ. AI/a | EFFICIENCY CUCUMBER Percent Control[a] Two-Spotted Mite | EFFICIENCY CUCUMBER Percent Control[a] Green Peach Aphid | COTTON Boll Weevils Percent[b] Control | COTTON Boll Weevils Percent Feeding Damage |
|---|---|---|---|---|---|
| Invention | 16 | — | 53% | — | — |
| | 4 | 94% | 30 | 98% | 7% |
| | 1 | 62 | 40 | 90 | 47 |
| | 0.25 | 51 | 39 | 68 | 62 |
| | 0.06 | 27 | — | 50 | 62 |
| | 0.015 | — | — | 0 | 97 |
| GUTHION 2L* | 16 | — | 55 | — | — |
| | 4 | 99 | 20 | 100 | 23 |
| | 1 | 99 | 27 | 90 | 43 |
| | 0.25 | 80 | 30 | 50 | 91 |
| | 0.06 | 52 | — | 44 | 85 |
| | 0.015 | — | — | — | 90 |
| GUTHION 50WP* | 16 | — | 0 | — | — |
| | 4 | 76 | 0 | 98 | 7 |
| | 1 | 56 | 0 | 93 | 7 |
| | 0.25 | 51 | 0 | 84 | 73 |
| | 0.06 | 10 | — | 45 | 92 |

|  | -continued | | | | |
|---|---|---|---|---|---|
|  | 0.015 | — | — | 0 | 97 |
| UNTREATED CONTROL |  | 0 | 0 | 0 | 100 |

| | PHYTOTOXICITY | |
|---|---|---|
| TREATMENT | LBS. AI/a | COTTON | CUCUMBER |
| Invention | 16 | 60% | 70% |
|  | 8 | 40 | 50 |
|  | 4 | 20 | 30 |
|  | 2 | 0 | 10 |
| GUTHION 2L | 16 | 90 | 98 |
|  | 8 | 60 | 70 |
|  | 4 | 60 | 40 |
|  | 2 | 40 | 30 |
| GUTHION 50WP | 16 | 20 | 50 |
|  | 8 | 3 | 30 |
|  | 4 | 0 | 10 |
|  | 2 | 0 | 10 |
| UNTREATED CONTROL |  | 0 | 0 |

[a] Based on Abbott formula
[b] Absolute
*products of Mobay Chemical Corporation EPA registration numbers 3125-102 and 3125-193-AA, respectively.

EXAMPLE 9

A composition was prepared in a manner similar to that of Example 3 except that 4.00 parts of the formulation without propylene glycol was combined with sufficient amounts of various organic solvent to yield dispersions containing 2 lb/gallon of Azinphos-methyl and the dispersions were evaluated.

| FORMULATION (4 parts Example 3 less solvent and)- | Azinphos-methyl solubility at 40° C. in ppm | Evaluation |
|---|---|---|
| 4.7 parts isopropylacetate |  | Crystallizes after 3 days −6° C. |
| 6.7 parts butyrolactone | >3.3 × 10⁵ | Crystallizes after 9 days −6° C. |
| 5.6 cyclohexane | >3.2 × 10⁵ | Crystallizes after 9 days −6° C. |
| 4.8 methylisobutylketone | >1.5 × 10⁵ | Crystallizes after 3 days −6° C. |
| 6.3 tetrahydrofurfuryl alcohol |  | Crystallizes after 3 days −6° C. |
| 7.5 glycerin | 5-10 × 10³ | Crystallizes after 3 days −6° C. |
| 5.7 methylcellosolve |  | Crystallizes after 3 days −6° C. |
| 6.6 Carbowax 200* | 1-2 × 10⁵ | Crystallizes after 3 days −6° C. |
| 6.1 Propylene glycol | 1.5 × 10⁴ | Long term stability |

*Polypropylene glycol $M_n$ = 200

It is believed that all the solvents other than glycerine have too high a solubility for the Azinphos-methyl for the particular combination of dispersant and diluents employed to suppress Ostwald ripening. In fact, for some of the solvents the Azinphos-methyl is entirely dissolved but the solution is unstable (butyrolactone and cyclohexane). The glycerine while it has a low solubility for the Azinphos-methyl it is evidently incompatible with impurities normally found in this chemical.

The solubility at 40° C. was selected as a characterizing parameter because it is believed that this temperature is typically reached during normal grinding operations to obtain to desired particle size distribution.

EXAMPLE 10

An insecticidal formulation was prepared by combining 4 parts of the following commercial available wettable powders with 6.14 parts of propylene glycol:

| WETTABLE POWDER | SOLUBILITY OF TECHNICAL IN PROPYLENE GLYCOL AT 40° C. IN PPM |
|---|---|
| Atrazine 80 WP | 5-10 × 10³ |
| Captan 50 | 75 × 10³ |
| Imidan 50 | — |

These dispersions were stable for 7 days at −6° C.

EXAMPLE 11

An insecticidal formulation was prepared by combining the following ingredients:

22.2 parts 3,5-dimethyl-4-(methylthio)phenol methyl carbamate
0.6 parts cellulose derivative thickening agent
4.2 parts talc
0.6 parts sodium lignosulfonate dispersant
1.45 parts sodium silicoaluminate; particle size average 12-20 microns mean surface area 180-225 m²/g
70.95 parts propylene glycol.

The dispersion was stable at room temperature for an extended period but displayed settling after 8 months. The active compound has a solubility of >2×10⁴ ppm at 40° C. and less than 1×10⁴ at 20° C.

The settling is believed to be due to the talc content and it is believed that its omission or replacement with a silica or clay would obviate this problem, e.g., by increasing the sodium silicoaluminate to 5.65 parts.

EXAMPLE 12

An insecticidal formulation was prepared by combining the following ingredients:

32.4 parts Propoxur
0.9 parts octylphenoxypolyethoxyethanol wetting agent with a hydrophilic lilophilic balance of 13.5
0.9 parts sodium lignosulfonate dispersant with a surface tension in 1% aqueous solution of 53 dyne/cm
0.2 parts soap
3.13 parts Barden clay non-absorptive diluent
6.71 parts of a fairly non-absorptive sodium silicoaluminate diluent with mean particle size of 12 to 20 millimicrons and an average surface area of 180 to 225 m²/g
0.45 parts citric acid.

This formulation had the following Coulter counter particle size distribution:

| 0–4 microns | 50% |
|---|---|
| 4–8 microns | 30% |
| 8–12 microns | 15% |
| >12 microns | 5% |

This formulation was combined with 53.1 parts of propylene glycol to form a dispersion and a similar dispersion was also prepared from this formulation and 53.1 parts of ethylene glycol. The former dispersion was still stable after 1 year's storage at about 20° C. and the latter was still stable after 4 month's storage under the same conditions.

The effectiveness of the former formulation against German roaches on unpainted wood was compared to that of a commercial 70% wettable powder formulation of Propoxur as follows:

| TREATMENT | DOSAGE | ROACH CONTROL | | | | | |
|---|---|---|---|---|---|---|---|
| | | Percent Roach Control After Initial (0 Day Residual) | | | | 1 week Residual | 2 weeks Residual |
| | | 0.5 hr. | 1 hr. | 2 hrs. | 24 hrs. | 24 hrs. | 24 hrs. |
| Invention | 1% | 60 | 73 | 87 | 100 | 88 | 8 |
| | 0.5 | 3 | 3 | 23 | 68 | 0 | — |
| | 0.25 | 0 | 0 | 0 | 0 | — | — |
| | 0.125 | 0 | 0 | 0 | 0 | — | — |
| Propoxur | 1 | 38 | 55 | 93 | 100 | 95 | 37 |
| | 0.5 | 0 | 0 | 8 | 53 | 3 | — |
| | 0.25 | 0 | 0 | 0 | 0 | — | — |
| | 0.125 | 0 | 0 | 0 | 0 | — | — |
| Untreated Control | | 0 | 0 | 0 | 0 | 0 | 0 |

APPLICATION ON UNPAINTED WOOD

The solubility of the Propoxur in ethylene glycol is in excess of $5 \times 10^3$ ppm at 4° C.

What is claimed is:

1. A flowable water dispersible pesticide formulation comprising
    (a) a finely divided biologically active water insoluble solid pesticide compound,
    (b) an organic water miscible solvent which has a solubility for said pesticide compound of between 1000 ppm and 10 wt. % at 40° C., and
    (c) a sufficient amount of finely divided inert filler and dispersant effective for dispersing water insoluble substances in aqueous media to maintain said compound in stable suspension in said organic solvent and prevent either agglomeration or Ostwald ripening.

2. A process for the production of stable suspensions or dispersions of biologically active pesticides in water compatible organic solvents in which the pesticide has significant solubility comprising
    (a) treating the pesticide to inactivate destabilizing impurities by purification or adsorption,
    (b) controlling the particle size of the pesticide to give a distribution with substantially no particles in excess of 12 microns with less than 40% of the particles having a size in excess of 8 microns,
    (c) mixing the pesticide with sufficient inert filler and dispersant to impart stability to the dispersion and prevent either agglomerization or Ostwald ripening, and
    (d) dispersing the pesticide in an organic solvent which has a solubility for said pesticide compound of between 1000 ppm and 10 wt. % at 40° C. and which is miscible with water.

3. A storage stable, flowable, water dispersible pesticide suspension comprising
    (a) between 10 and 50 wt. % of a finely divided biologically active compound with limited solubility in or chemical sensitivity to water, which is solid at temperatures below about 50° C.,
    (b) an organic solvent which is liquid at temperatures above about −20° C., which has a vapor pressure less than water, and which has a solubility for said active compound of between 1000 ppm and 10 wt. % at 40° C., and
    (c) sufficient ion bearing solid dispersant and inert solid filler to maintain the suspensions stable for at least 3 days at −5° C.,
said suspension having a viscosity of between about 400 and 5000 cps at 20° C. and having said organic solvent as the continuous phase.

4. A process of preparing a flowable, storage stable, water dispersible pesticide suspension in an organic solvent comprising
    (a) size reducing a biologically active compound which is solid at temperatures below 50° C. so that no more than about 5% of the particles are in excess of 12 microns,
    (b) combining said active compound with sufficient solid inert adsorptive filler to provide adsorptive capacity for any of said active compound which melts during size reduction and for any low melting point impurities admixed with said active compound as a result of its synthesis,
    (c) adding sufficient non-adsorptive solid inert filler and solid ion bearing dispersant to assure that the total suspension remains stable for at least 3 days at −5° C., and
    (d) suspending these solids in an amount of an organic solvent, which is liquid at temperatures above about −20° C., which has a vapor pressure less than water, and which has a solubility for said active compound of between 1000 ppm and 10 wt. % at 40° C.; sufficient solvent being used to provide at least 2.5 parts per 100 suspension of said active compound and to provide the suspension with a viscosity between 400 and 5000 cps at 20° C.

5. A storage stable, flowable, water emulsifiable pesticide suspension comprising
    (a) at least 2.5 parts per 100 of the total suspension of a biologically active pesticidal compound which is a solid at temperatures below about 50° C. and which has a particle size distribution with no more than 5% in excess of 12 microns, sufficient compound being present to exceed the solubility limit of the suspending medium at 40° C.,
    (b) an organic solvent which is the continuous phase of the suspension, which is liquid at temperatures in excess of −20° C., which is chemically inert to said active compound, which has a vapor pressure less than that of water and which has a solubility for said active compound of between 1000 ppm and 10 wt. % at 40° C., sufficient solvent being present to provide the suspension with a viscosity between 400 and 5000 cps at 20° C.,
    (c) an ion bearing dispersant which is solid at temperatures below 50° C., which has a particle size distribution with less than 5% in excess of 12 microns, and which is chemically inert to both said compound and said solvent, sufficient dispersant being present to prevent agglomeration of said active compound particles and suppress particle growth by dissolution and recrystallization of said active compound, and (d) inert fillers which are solid at temperatures below 50° C., which are substantially insoluble in said solvent, which are chemically inert to said active compound, said solvent and said dispersant, and which have an adsorptive capacity sufficient to adsorb any liquid other than said solvent present in the suspension, sufficient inert filler being present to maintain the stability of the suspension against separation for at least 3 days at −5° C.

6. A storage stable, flowable, water dispersible suspension of Azinphos-methyl in propylene glycol having a viscosity after agitation of between 400 and 5000 cps at 20° C. and containing sufficient dispersant and inert filler to maintain the stability of the suspension at temperatures between 40° and 0° C.

7. The suspension of claim 6 wherein the dispersant is an alkali metal lignosulfonate.

8. A storage stable, flowable, water dispersible pesticide suspension comprising:

(a) about 15.0 to 45.0 parts Azinphos-methyl,
(b) about 5 to 10 parts of a sodium silica aluminate diluent with a surface area of 180 to 225 m$^2$/g,
(c) about 0 to 3 parts of a non-adsorptive amorphous silica diluent with a surface area of less than about 14,000 cm$^2$/g,
(d) about 1 to 5 parts of kaolin clay,
(e) about 0.5 to 3 parts of the sugar-free sodium based sulfonates of kraft lignin,
(f) about 0 to 3 parts of a sodium isopropyl naphthalene sulfonate wetting agent, and
(g) sufficient propylene glycol to give a concentration of 1.75 to 4.5 pounds of Azinphos-methyl per gallon of suspension, said suspension having a viscosity after agitation to dispel any thixotropic gelling of between about 400 and 5000 cps at 20° C. and being stable at temperatures of 40° and 0° C. as well as cycling there between for at least one year.

9. The suspension of claim 8 wherein the solid ingredients have a Coulter counter particle size distribution as follows:

| | |
|---|---|
| 0–4 microns | 50 to 90% |
| 4–8 microns | 10% to 40% |
| 8–12 microns | no more than 10% |
| >12 microns | less than 2%. |

* * * * *